(12) United States Patent
Hallinan et al.

(10) Patent No.: US 6,344,483 B1
(45) Date of Patent: Feb. 5, 2002

(54) HALOGENATED AMIDINO AMINO ACID DEVIRATIVES USEFUL AS NITRIC OXIDE SYNTHASE INHIBITORS

(75) Inventors: E. Ann Hallinan, Evanston; Barnett S. Pitzele, Skokie; Dale P. Spangler, Deerfield, all of IL (US); Mihaly V. Toth, St. Louis; R. Keith Webber, St. Charles, both of MO (US); Arija A. Bergmanis, Des Plaines, IL (US); Timothy J. Hagen, Gurnee, IL (US); Sofya Tsymbalov, Des Plaines, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/402,953
(22) PCT Filed: Mar. 4, 1999
(86) PCT No.: PCT/US99/03728
§ 371 Date: Jan. 31, 2000
§ 102(e) Date: Jan. 31, 2000
(87) PCT Pub. No.: WO99/46240
PCT Pub. Date: Sep. 16, 1999

(51) Int. Cl.[7] .................. A61K 31/195; C07C 259/00; C07C 61/16; C07C 229/00

(52) U.S. Cl. ................. 514/564; 514/565; 514/568; 514/572; 562/437; 562/438; 562/440; 562/506; 562/507; 562/556; 562/561; 562/562; 562/586

(58) Field of Search ................. 562/437, 438, 562/440, 506, 507, 556, 561, 562, 586; 514/564, 565, 568, 572

(56) References Cited

U.S. PATENT DOCUMENTS 5,981,511 A * 11/1999 Gapud et al. .................. 514/63

FOREIGN PATENT DOCUMENTS

| WO | WO93/13055 | 7/1993 |
| WO | WO95/00505 | 1/1995 |
| WO | WO95/34534 | 12/1995 |
| WO | WO96/19440 | 6/1996 |
| WO | WO97/32844 | 9/1997 |

* cited by examiner

Primary Examiner—Gary Geist
Assistant Examiner—Leigh C. Maier
(74) Attorney, Agent, or Firm—Philip B. Polster, II; G. D. Searle & Co.

(57) ABSTRACT

The current invention discloses halogenated amidino amino acid derivatives useful as nitric oxide synthase inhibitors, and pharmaceutically acceptable salts thereof.

12 Claims, No Drawings

HALOGENATED AMIDINO AMINO ACID DEVIRATIVES USEFUL AS NITRIC OXIDE SYNTHASE INHIBITORS

This is the National Stage entry under 35 USC 371 of PCT/US99/03728, filed Mar. 4, 1999.

BACKGROUND OF THE INVENTION

1. Field of the Invention

The present invention relates to halogenated amidino amino acid derivatives and their use in therapy, in particular their use as nitric oxide synthase inhibitors.

2. Discussion of the Prior Art

It has been known since the early 1980's that the vascular relaxation caused by acetylcholine is dependent on the presence of the vascular endothelium and this activity was ascribed to a labile humoral factor termed endothelium-derived relaxing factor (EDRF). The activity of nitric oxide (NO) as a vasodilator has been known for well over 100 years. In addition, NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme NO synthase.

Nitric oxide is the endogenous stimulator of the soluble guanylate cyclase. In addition to endothelium-dependent relaxation, NO is involved in a number of biological actions including cytotoxicity of phagocytic cells and cell-to-cell communication in the central nervous system (see Moncada et al., Biochemical Pharmacology, 38, 1709–1715, 1989; Moncada et al., Pharmacological Reviews, 43, 109–142, 1991). Excess NO production appears to be involved in a number of pathological conditions, particularly conditions which involve systemic hypotension such as toxic shock, septic shock and therapy with certain cytokines (Kerwin et al., J. Medicinal Chemistry, 38, 4343–4362, 1995).

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, Ca++/calmodulin dependent enzyme, located in the endothelium, that releases NO in response to receptor or physical stimulation.

(ii) a constitutive, Ca++/calmodulin dependent enzyme, located in the brain, that releases NO in response to receptor or physical stimulation.

(iii) a Ca++ independent enzyme which is induced after activation of vascular smooth muscle, macrophages, endothelial cells, and a number of other cells by endotoxin and cytokines. Once expressed this inducible NO synthase generates NO continuously for long periods.

The NO released by the two constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase (Knowles and Moncada, Biochem J., 298, 249–258, 1994 Billiar et al., Annals of Surgery, 221, 339–349, 1995; Davies et al., 1995).

There is also a growing body of evidence that NO may be involved in the degeneration of cartilage which takes place in certain conditions such as arthritis and it is also known that NO synthesis is increased in rheumatoid arthritis and in osteoarthritis (McInnes et al., J. Exp. Med, 184, 1519–1524, 1996; Sakurai et al., J. Clin. Investig., 96, 2357–2363, 1995).

Accordingly, conditions in which there is an advantage in inhibiting NO production from L-arginine include autoimmune and/or inflammatory conditions affecting the joints, for example arthritis, and also inflammatory bowel disease, cardivascular ischemia, diabetes, diabetic retinopathy, nephropathy, cardiomyopathy, congestive heart failure, myocarditis, atherosclerosis, migraine, reflux esophagitis, diarrhea, irritable bowel syndrome, cystic fibrosis, emphysema, asthma, chronic obstructive pulmonary disease, bronchiectasis, herniated vertebral discs, obesity, psoriasis, rosacea, contact dermatitis, hyperalgesia (allodynia), cerebral ischemia [both focal ischemia, thrombotic stroke and global ischemia (secondary to cardiac arrest)], anxiety multiple sclerosis and other central nervous system disorders mediated by NO, for example Parkinson's disease and Alzheimer's disease, rhinitis, cancer therapy, and other disorders mediated by NO including opiate tolerance in patients needing protracted opiate analgesics, and benzodiazepine tolerance in patients taking benzodiazepines, and other addictive behavior, for example, nicotine and eating disorders (Kerwin et al., J. Medicinal Chemistry, 38, 4343–4362, 1995; Knowles and Moncada, Biochem J., 298, 249–258, 1994; Davies et al., 1995; Pfeilschifter et al., Cell Biology International, 20, 51–58, 1996).

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy (E. Kelly et al., J. Partent. Ent. Nutri., 19, 234–238, 1995; S. Moncada and E. Higgs, FASEB J., 9, 1319–1330, 1995; R. G. Kilbourn et al, Crit. Care Med., 23, 1018–1024, 1995).

More recently, NO has been identified as being a neurotransmitter in pain pathways of the spinal cord. The administration of NO synthase inhibitors in patients with cronic pain syndromes, and more specifically cronic tension-type headaches, has been shown to reduce the level of pain. (The Lancet, 353:256–257, 287–289, 1999)

Some of the NO synthase inhibitors proposed for therapeutic use so far, and in particular L-NMMA, are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E.

Higgs, FASEB J., 9, 1319–1330, 1995). WO 96/35677, WO 96/33175, WO 96/15120, WO 95/11014, WO 95/11231 WO 95/25717, WO 95/24382, WO94/12165, WO94/14780, WO93/13055, EP0446699A1 and U.S. Pat. No. 5,132,453 disclose compounds that inhibit nitric oxide synthesis and preferentially inhibit the inducible isoforms of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering.

The present invention is directed to the halogenation of amidino amino acid derivatives to exhibit iNOS inhibition activity and bioactivity. Halogenation alters the basicity of the amidine moiety, and increases potency and provides a longer half-life in vivo as iNOS inhibitors.

Compounds of the present invention are represented by halogenated amidino compounds of formula (I):

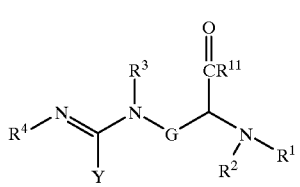

or a pharmaceutically acceptable salt thereof, wherein:

$R^1$ is selected from the group consisting of hydrogen, $C_1$–$C_{10}$ alkyl, $C_2$–$C_{10}$ alkenyl, and $C_2$–$C_{10}$ alkynyl;

$R^2$ is selected from the group consisting of hydrogen, $C_1$–$C_{10}$ alkyl, $C_2$–$C_{10}$ alkenyl, $C_2$–$C_{10}$ alkynyl, and either R or S alpha-amino acid;

$R^3$ and $R^4$ are independently selected from the group consisting of hydrogen, $C_1$–$C_{10}$ alkyl, $C_2$–$C_{10}$ alkenyl, $C_2$–$C_{10}$ alkynyl, and $NO_2$;

wherein $R^1$, $R^2$, $R^3$ and $R^4$ can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, and guanidino;

$R^{11}$ is selected from the group consisting of hydroxyl and R or S alpha-amino acid;

G is selected from the group consisting of $C_1$–$C_{10}$ alkylene, $C_2$–$C_{10}$ alkenylene, and $C_2$–$C_{10}$ alkynylene, each of which is optionally substituted with one or more selected from the group consisting of halogen, hydroxy, trifluoromethyl, nitro, cyano, amino, $C_1$–$C_{10}$ alkyl, $=CH_2$, $C_2$–$C_{10}$ alkenyl, $C_2$–$C_{10}$ alkynyl, and $C_1$–$C_{10}$ alkoxy, each of which can be can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

G is selected from the formula $(CH_2)_p$—$(CX^1X^2)_r$—$(CH_2)_s$—Q—$(CH_2)_t$—$(CX^3X^4)_u$—$(CH_2)_v$ where p, r, s, t, u, v are independently 0 to 3 and Q is oxygen, $C=O$, $S(O)_a$ wherein a is 0 to 2, with the proviso that when a is 1 or 2, G must contain halogen, or $NR^{12}$ wherein $R^{12}$ is hydrogen or $C_1$–$C_{10}$ alkyl which may be optionally substituted with one or more selected from the group consisting of $C_1$–$C_{10}$ alkyl, $C_1$–$C_{10}$ alkoxy, hydroxy, trifluoromethyl, nitro, cyano, amino, and halogen;

G is selected from the formula —$(CH_2)_w$—$(CX^5X^6)_y$—$(CH_2)_z$—A—$(CH_2)_k$—$(CX^7X^8)_j$—$(CH_2)_h$ wherein w, y, z, k, j, h are independently 0 to 3 and A is a 3 to 6 membered carbocyclic radical or heterocyclic radical which may be optionally substituted with one or more selected from the group consisting of halogen, $C_1$–$C_{10}$ alkyl, $C_1$–$C_{10}$ alkoxy, hydroxy, trifluoromethyl, nitro, cyano, and amino, each of which may be optionally substituted with halogen or $C_1$–$C_{10}$ alkyl, with the proviso that when G is selected from the formula —$(CH_2)_w$—$(CX^5X^6)_y$—$(CH_2)_z$—A—$(CH_2)_k$—$(CX^7X^8)_j$—$(CH_2)_h$, Y must contain halogen;

$X^1$, $X^2$, $X^3$, $X^4$, $X^5$, $X^6$, $X^7$, $X^8$ are independently not present, hydrogen, halogen, $C_1$–$C_{10}$ alkyl, $=CH_2$, $C_2$–$C_{10}$ alkenyl, or $C_2$–$C_{10}$ alkynyl, wherein $C_1$–$C_{10}$ alkyl, $=CH_2$, $C_2$–$C_{10}$ alkenyl, and $C_2$–$C_{10}$ alkynyl can be optionally substituted with one or more from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

Y is selected from the group consisting of heterocycle, $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl, each of which is optionally substituted with one or more selected from the group consisting of halogen, hydroxy, trifluoromethyl, nitro, cyano, amino, $C_1$–$C_{10}$ alkyl, $C_2$–$C_{10}$ alkenyl, $C_2$–$C_{10}$ alkynyl, and $C_1$–$C_{10}$ alkoxy;

Y can be $NR^9R^{10}$ wherein $R^9$ and $R^{10}$ are independently selected from the group consisting of hydrogen, $C_1$–$C_{10}$ alkyl, $C_3$–$C_1$1 cycloalkyl, $C_2$–$C_{10}$ alkenyl, $C_2$–$C_{10}$ alkynyl, nitro, amino, aryl, and $C_1$–$C_{10}$ alkaryl;

with the proviso that at least one of G or Y contains a halogen.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

It is an object of the present invention to provide compounds that have usefulness as inhibitors of nitric oxide synthase. These compounds also preferentially inhibit the inducible form over the constitutive form by at least 3 fold.

It is also an object of the present invention to provide compounds that are more selective than those known in the art.

DETAILED DESCRIPTION OF THE INVENTION

Preferably, compounds of the present invention are halogenated amidino compounds of formula (I) wherein:

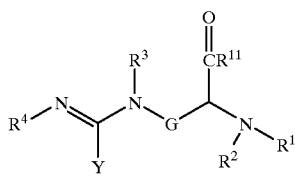

(I)

or a pharmaceutically acceptable salt thereof, wherein:

$R^1$ is selected from the group consisting of hydrogen, $C_1$–$C_{10}$ alkyl, $C_2$–$C_{10}$ alkenyl, and $C_2$–$C_{10}$ alkynyl;

$R^2$ is selected from the group consisting of hydrogen, $C_1$–$C_{10}$ alkyl, $C_2$–$C_{10}$ alkenyl, $C_2$–$C_{10}$ alkynyl, and either R or S alpha-amino acid;

$R^3$ and $R^4$ are independently selected from the group consisting of hydrogen, $C_1$–$C_{10}$ alkyl, $C_2$–$C_{10}$ alkenyl, $C_2$–$C_{10}$ alkynyl, and $NO_2$;

wherein $R^1$, $R^2$, $R^3$ and $R^4$ can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, and guanidino;

$R^{11}$ is selected from the group consisting of hydroxyl and R or S alpha-amino acid;

G is selected from the group consisting of $C_1$–$C_{10}$ alkylene, $C_2$–$C_{10}$ alkenylene, and $C_2$–$C_{10}$ alkynylene, each of which is optionally substituted with one or more selected from the group consisting of halogen, hydroxy, trifluoromethyl, nitro, cyano, amino, $C_1$–$C_{10}$ alkyl, $=CH_2$, $C_2$–$C_{10}$ alkenyl, $C_2$–$C_{10}$ alkynyl, and $C_1$–$C_{10}$ alkoxy, each of which can be can be optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

G is selected from the formula $(CH_2)_p$—$(CX^1X^2)_r$—$(CH_2)_s$—Q—$(CH_2)_t$—$(CX^3X^4)_u$—$(CH_2)_v$, where p, r, s, t, u, v are independently 0 to 3 and Q is oxygen, C=O, $S(O)_a$ wherein a is 0 to 2, with the proviso that when a is 1 or 2, G must contain halogen, or $NR^{12}$ wherein $R^{12}$ is hydrogen or $C_1$–$C_{10}$ alkyl which may be optionally substituted with one or more selected from the group consisting of $C_1$–$C_{10}$ alkyl, $C_1$–$C_{10}$ alkoxy, hydroxy, trifluoromethyl, nitro, cyano, amino, and halogen;

G is selected from the formula —$(CH_2)_w$—$(CX^5X^6)_y$—$(CH_2)_z$—A—$(CH_2)_k$—$(CX^7X^8)_j$—$(CH_2)_h$ wherein w, y, z, k, j, h are independently 0 to 3 and A is a 3 to 6 membered carbocyclic radical or heterocyclic radical which may be optionally substituted with one or more selected from the group consisting of halogen, $C_1$–$C_{10}$ alkyl, $C_1$–$C_{10}$ alkoxy, hydroxy, trifluoromethyl, nitro, cyano, and amino, each of which may be optionally substituted with halogen or $C_1$–$C_{10}$ alkyl, with the proviso that when G is selected from the formula —$(CH_2)_w$—$(CX^5X^6)_y$—$(CH_2)_z$—A—$(CH_2)_k$—$(CX^7X^8)_j$—$(CH_2)_h$, Y must contain halogen;

$X^1$, $X^2$, $X^3$, $X^4$, $X^5$, $X^6$, $X^7$, $X^8$ are independently not present, hydrogen, halogen, $C_1$–$C_{10}$ alkyl, $=CH_2$, $C_2$–$C_{10}$ alkenyl, or $C_2$–$C_{10}$ alkynyl, wherein $C_1$–$C_{10}$ alkyl, $=CH_2$, $C_2$–$C_{10}$ alkenyl, and $C_2$–$C_{10}$ alkynyl can be optionally substituted with one or more from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

Y is selected from the group consisting of heterocycle, $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl, each of which is optionally substituted with one or more selected from the group consisting of halogen, hydroxy, trifluoromethyl, nitro, cyano, amino, $C_1$–$C_{10}$ alkyl, $C_2$–$C_{10}$ alkenyl, $C_2$–$C_{10}$ alkynyl, and $C_1$–$C_{10}$ alkoxy;

Y can be $NR^9R^{10}$ wherein $R^9$ and $R^{10}$ are independently selected from the group consisting of hydrogen, $C_1$–$C_{10}$ alkyl, $C_3$–$C_{10}$ cycloalkyl, $C_2$–$C_{10}$ alkenyl, $C_2$–$C_{10}$ alkynyl, nitro, amino, aryl, and $C_1$–$C_{10}$ alkaryl;

with the proviso that at least one of G or Y contains a halogen.

More preferably, compounds of the present invention are of the formula (I) wherein;

G is selected from the formula $(CH_2)_p$—$(CX^1X^2)_r$—$(CH_2)_s$—Q—$(CH_2)_t$—$(CX^3X^4)_u$—$(CH_2)$, where p, r, s, t, u, v are independently 0–3 and Q is oxygen, C=O, $S(O)_a$ wherein a is 0 to 2, with the proviso that when a is 1 or 2, G must contain a halogen, or $NR^{12}$ wherein $R^{12}$ is hydrogen or $C_1$–$C_{10}$ alkyl, which may be optionally substituted with one or more selected from the group consisting of $C_1$–$C_{10}$ alkyl, $C_1$–$C_{10}$ alkoxy, hydroxy, trifluoromethyl, nitro, cyano, amino, and halogen; and Y is selected from the group consisting of $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl.

More preferably, compounds of the present invention are of the formula (I):

wherein:

$R^1$, $R^2$ are H, $R^3$, $R^4$ are independently H, or $NO_2$;

G is selected from the formula $(CH_2)_p$—$(CX^1X^2)_r$—$(CH_2)_s$—Q—$(CH_2)_t$—$(CX^3X^4)_u$—$(CH_2)_v$ where p, r, s, t, u, v are independently 0–3 and Q is oxygen, C=O, $S(O)_a$ wherein a is 0 to 2, with the proviso that when a is 1 or 2, G must contain a halogen, or $NR^{12}$ wherein $R^{12}$ is hydrogen or $C_1$–$C_{10}$ alkyl, which may be optionally substituted with one or more selected from the group consisting of $C_1$–$C_{10}$ alkyl, $C_1$–$C_{10}$ alkoxy, hydroxy, trifluoromethyl, nitro, cyano, amino, and halogen; and Y is selected from the group consisting of $C_1$–$C_6$ alkyl, $C_3$–$C_6$ cycloalkyl, $C_2$–$C_6$ alkenyl, and $C_2$–$C_6$ alkynyl, each of which is optionally substituted with one or more halogens, or $NHR^9$ wherein $R^9$ is hydrogen, $C_1$–$C_6$ alkyl $C_3$–$C_6$ cycloalkyl, $C_2$–$C_6$ alkenyl, or $C_2$–$C_6$ alkynyl.

More preferably, compounds of the present invention are of the formula (I):

wherein:

$R^1$, $R^2$, $R^3$ and $R^4$ are H; and

Y is $C_1$–$C_6$ alkyl optionally substituted with at least one halogen.

Most preferably, compounds of the present invention are selected from the group consisting of:

N-(2-fluoro-1-iminoethyl)-3-aminoethyl-L-cysteine dihydrochloride;

N-(2-fluoro-1-iminoethyl)-2-aminoethyl-L-cysteine dihydrochloride;

N-(2-fluoro-1-iminoethyl)-2-aminoethyl-D,L-homocysteine dihydrochloride; and

N-(2-fluoro-1-iminoethyl)-2-aminoethyl-L-homocysteine dihydrochloride.

As utilized herein, the term "alkyl", alone or in combination, means a branched or unbranched acyclic alkyl radical containing from 1 to 10, preferably from 1 to 8 carbon atoms and more preferably 1 to 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl" refers to a branched or unbranched unsaturated acyclic hydrocarbon radical in so much as it contains at least one double bond. Such radicals containing from 2 to 10 carbon atoms, preferably from 2 to 8 carbon atoms and more preferably 2 to 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "alkynyl" refers to a branched or unbranched unsaturated acyclic hydrocarbon radical in so much as it contains one or more triple bonds. Such radicals containing 2 to 10 carbon atoms, preferably having from 2 to 8 carbon atoms and more preferably having 2 to 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic radical" means an unsaturated cyclic hydrocarbon radical with 3 to about 6 carbon atoms, wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "aryl" means an aromatic hydrocarbon radical of 4 to 16 carbon atoms, preferably 6 to about 12 carbon atoms, more preferably 6 to 10 carbon atoms. Examples of suitable aromatic hydrocarbon radicals include phenyl, naphthyl, and the like.

The terms "cycloalkyl" or "cycloalkenyl" means an "alicyclic radical in a ring with 3 to 10 carbon atoms, and preferably from 3 to 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "alkylene" refers to hydrocarbons containing 1 to 10 carbon atoms, preferably 1 to 8 carbon atoms, and more preferably 1 to 6 carbon atoms.

The term "alkenylene" and "alkynylene" refers to hydrocarbons containing 2 to 10 carbon atoms, preferably 2 to 8 carbon atoms, and more preferably 2 to 6 carbon atoms.

The term "halogen" means fluorine, chlorine, bromine or iodine.

The term "prodrug" refers to a compound that is made more active in vivo.

As used herein, reference to "treatment" of a patient is intended to include prophylaxis.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), via inhalation rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

All references, patents or applications, U.S. or foreign, cited in the application are hereby incorporated by reference as if written herein.

The following are general synthetic sequences which are useful in making the compounds of the present invention.

Scheme 1

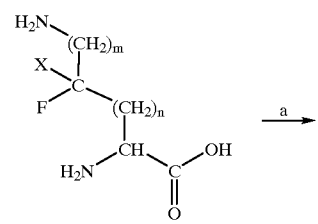

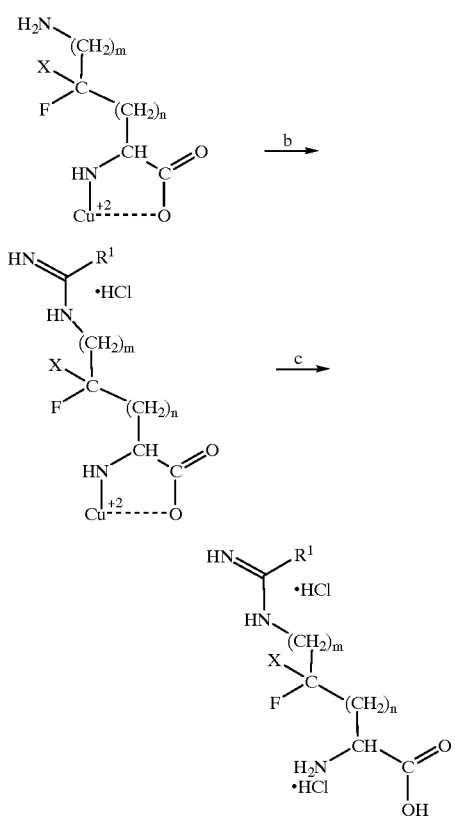

a. $CuSO_4$. b. $R^1C(=NH)OEt \cdot HCl$. c. ion exchange resin

Scheme 2

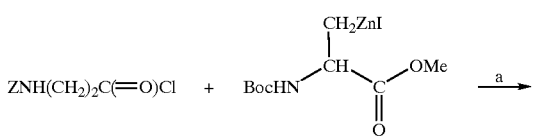

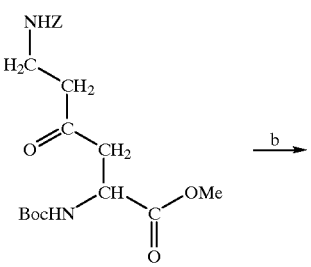

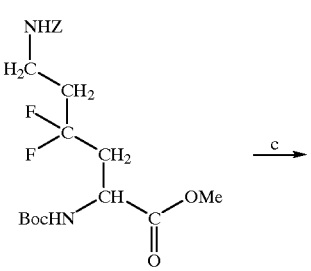

Scheme 5
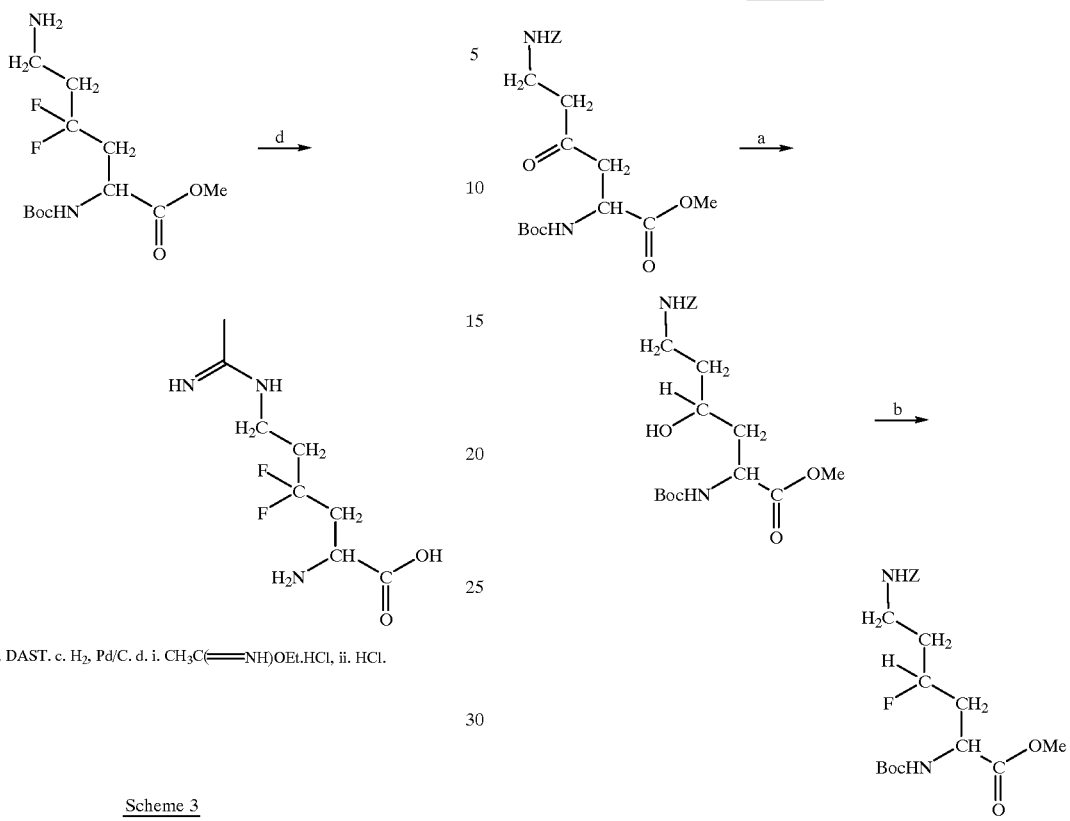
a. NaBH₄. b. DAST
a. (Ph₃P)₂PdCl₂. b. DAST. c. H₂, Pd/C. d. i. CH₃C(═NH)OEt·HCl, ii. HCl.
Scheme 3
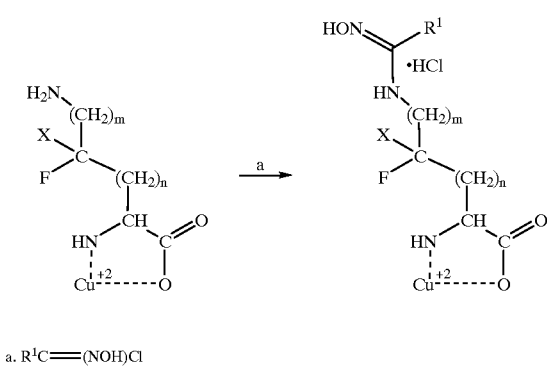
a. R¹C═(NOH)Cl
Scheme 6
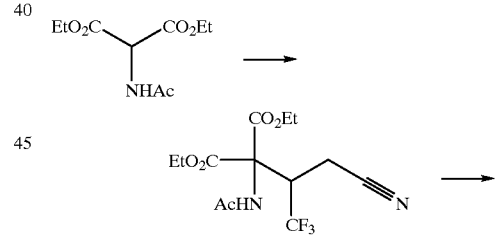
Scheme 4
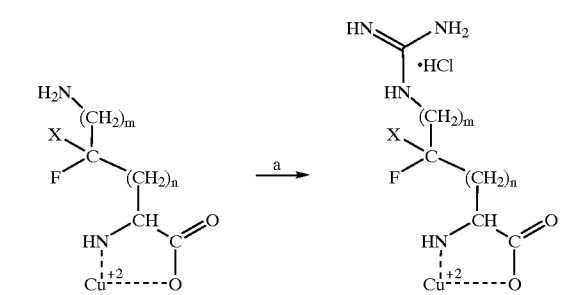
a. 3,5-dimethylpyrazole-1-carboxamidine
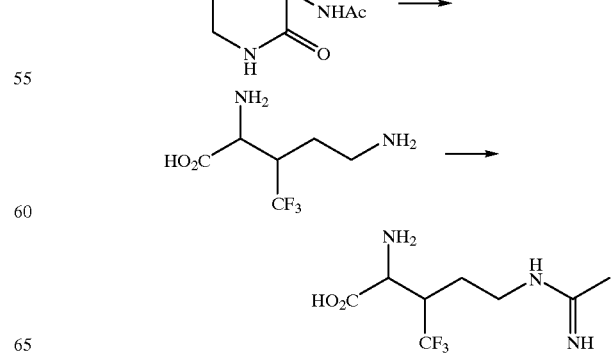

Scheme 7

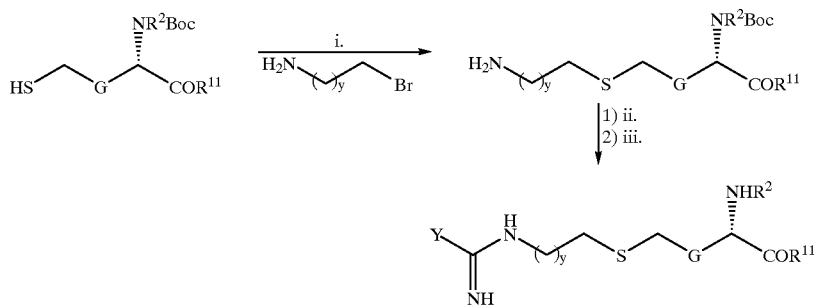

i. NaH
ii. YC(NH)OEt
iii. HCl

Scheme 8

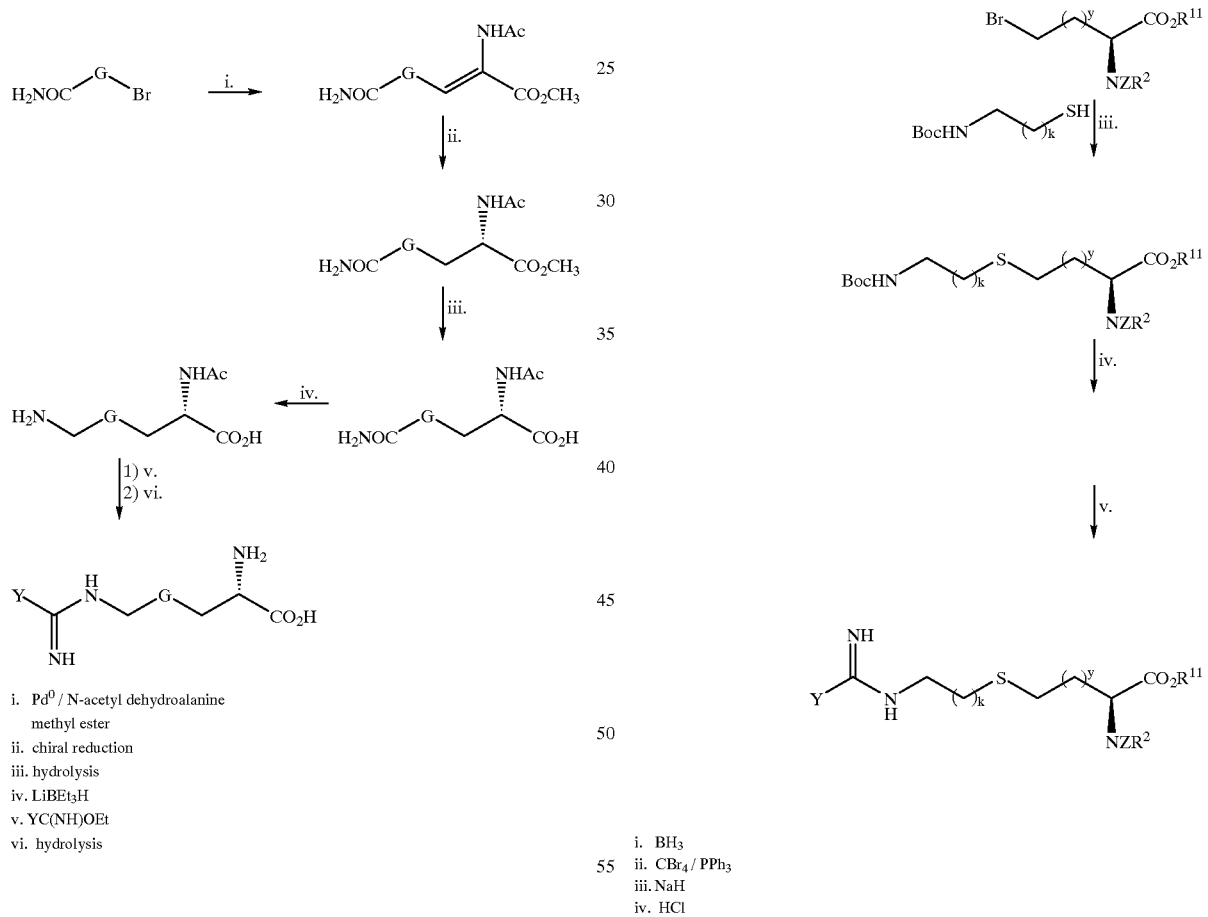

i. Pd⁰ / N-acetyl dehydroalanine methyl ester
ii. chiral reduction
iii. hydrolysis
iv. LiBEt$_3$H
v. YC(NH)OEt
vi. hydrolysis i. BH$_3$
ii. CBr$_4$ / PPh$_3$
iii. NaH
iv. HCl
v. YC(NH)OEt Scheme 9

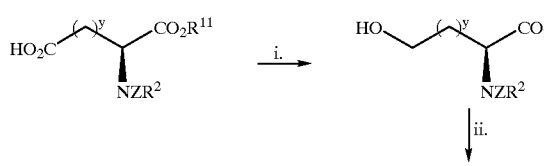

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

EXAMPLES

Example 1

4,4-difluoro-$N^5$-(1-iminoethyl)-L-ornithine dihydrochloride

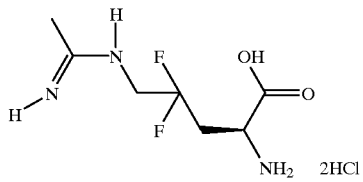

4,4-difluoro-ornithine is prepared as described in *J. Org. Chem.* 61, 1996, pp 2497–2500 and then treated in the same manner as described in *J. Antibiotics* 25, 1972, p 179 to form its copper complex. The copper complex of 4,4-difluoro-ornithine is treated with ethyl acetimidate hydrochloride as described in *Analytical Biochemistry* 62, 1974, p 291 to form the delta amidine. The copper complex is then broken up as described in *J. Antibiotics* 25, 1972, p 179 to form the title compound.

Example 2

4,4-difluoro-$N^6$-(1-iminoethyl)-L-lysine dihydrochloride

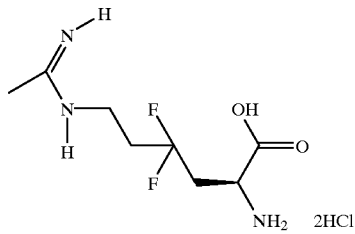

Boc-L-Ala(ZnI)-OMe is reacted with Z-beta-Ala-Cl under conditions described in *J. Org Chem* 57, 1992, pp 3397–3404 to give a protected 4-keto-L-lysine which is then dissolved in DCM and treated with DAST to yield protected 4,4-difluoro-L-lysine. The epsilon carbobenzoxy protecting group is then removed under catalytic hydrogenolysis conditions. The resulting compound is reacted with methyl acetimidate hydrochloride to yield the epsilon amidine which was then reacted with 2 N HCl to give the title compound.

Example 3

5,5-difluoro-$N^6$-(1-iminoethyl)-L-lysine dihydrochloride

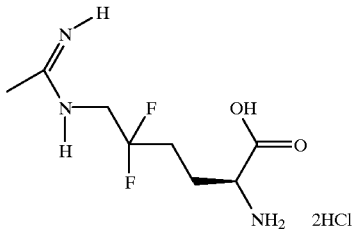

5,5-difluoro-lysine is prepared as described in *J. Med. Chem.* 20, 1977, pp 1623–1627 and then is treated in the same manner as described in *J. Antibiotics* 25, 1972, p 179 to form its copper complex. The copper complex of 5,5-difluoro-lysine is treated with ethyl acetimidate hydrochloride as described in *Analytical Biochemistry* 62, 1974, p 291 to form the epsilon amidine. The copper complex is then broken up as described in *J. Antibiotics* 25, 1972, p 179 to form the title compound.

Example 4

$N^6$-(2,2,2-trichloro-1-iminoethyl)-L-lysine dihydrochloride

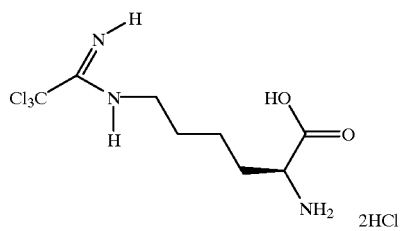

Ex-4a) A three-necked flask was charged with 10 mL of dimethylformamide and 0.26 g (0.001 mol) of α-N-Boc-L-Lys-OMe. To this solution was added 0.35 g (0.002 mol) of methyl trichloroacetimidate and 0.53 mL (0.003 mol) of diisopropylethylamine. This solution was allowed to stir and warm to 25 C. overnight. Concentration in vacuo removed the dimethylformamide. The residue was treated with trifluoroacetic acid for thirty minutes. This was diluted with water and purified via C-18 chromatography to afford 0.24 g (80%) of Ex-4a. FAB Mass Spectra, M+H =304.

Ex-4b) To a flask containing 0.12 g of Ex-4a was added 10 mL of methanol and 5 mL of 1N lithium hydroxide. This mixture was stirred for 10 minutes and then concentrated in vacuo. This material was purified via C-18 chromatography to afford 0.1 g (95%) of the title compound. FAB Mass Spectra, M+H=290.

Example 5

N[6]-(2,2,2-trifluoro-1-iminoethyl)-L-lysine dihydrochloride

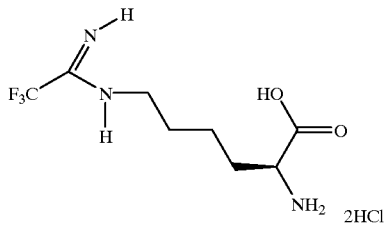

Ex-5a) A three-necked flask was fitted with a dry-ice/acetone condenser and charged with 100 mL of ethanol and 6.5 g (0.027 mol) of a-N-Boc-L-Lys-OH. This was cooled to −78° C. and 5 g (0.053 mol) of trifluoroacetonitrile was added via a gas dispersion tube. After addition was complete, 2.7 g (0.027 mol) of triethylamine was added. This solution was allowed to stir and warm to 25 C. overnight. Concentration in vacuo afforded 11 g of 5a as a colorless viscous oil. $^1$H-NMR($D_2O$) 1.05 (t, 9H), 1.25–1.75 (m, 6H), 1.35 (s, 9H), 2.8 (q, 6H), 2.95 (t, 2H), 3.7 (t, 1H); $^{19}$F-NMR ($D_2O$) −68.9 (s): Mass Spectra, M+Li=348.

Ex-5b) To a flask containing 0.5 g of Ex-5a was added 10 mL of dioxane (saturated with HCl). This mixture was stirred for 30 minutes and then concentrated in vacuo to afford a sticky white foam. This material was dissolved in water and lyophilized to afford the title compound as a hygroscopic foam. $^1$H-NMR($D_2O$) 1.15 (t, triethylamine hydrochloride), 1.3–1.5 (m, 2H), 1.6–1.7 (m, 2H), 1.8–1.9 (m, 2H), 3.05 (q, triethylamine hydrochloride), 3.35 (t, 2H), 3.9 (t, 1H); $^{19}$F-NMR ($D_2O$) −71.4 (s): Mass Spectra, M+H=242.

Example 6

N[6]-(2,2-difluoro-1-iminoethyl)-L-lysine dihydrochloride

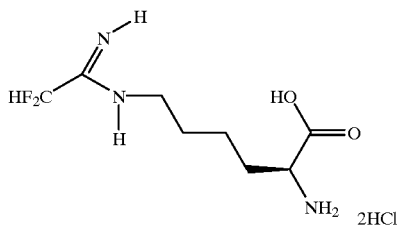

Ex-6a) To a mixture of methanol and a catalytic amount of palladium black was added 0.5 g (1.4 mmol) of the product of example Ex-20a. To this mixture was added an excess of ammonium formate. This was stirred at room temperature for 24 hours. The reaction mixture was filtered through celite and concentrated to afford a colorless oil.

Ex-6b) The product of Ex-6a dissolved in 2 N HCl and allowed to stir at room temperature for three hours. This solution was diluted with water and lyophilized to afford 0.3 g (95%) of the title product as a colorless oil.

$^1$H-NMR($D_2O$) 1.3–1.6 (m, 2H), 1.6–1.75 (m, 2H), 1.8–2.0 (m, 2H), 3.35 (t, 2H), 4.0 (t, 1H), 6.55 (t, 1H); Elemental analysis calcd. for $C_8H_{15}O_2N_3Cl_2F_2$+5$H_2O$+4 $NH_4Cl$+0.4 lysine: C, 18.16; H, 7.24; N, 15.88 Found: C, 18.13; H, 6.99; N, 15.69

Example 7

(±)-E-2-Amino-6-(1-imino-2-fluoroethylamino)-hex-4-enoicacid dihydrochloride

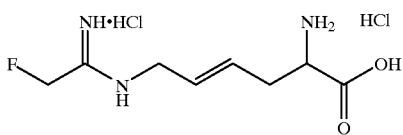

Ex-7a) Under argon, to 65.8 g of trans-1,4-dichloro-2-butene was added in portions 47 g of potassium phthalimide with mechanical stirring maintaining the temperature between 100° C. and 110° C. The reaction mixture was then stirred for 2 h keeping the temperature between 145° C. to 150° C. It was then cooled to 20° C. and extracted with 3×400 mL of ether. The ether layer was separated and stripped to give a solid. This solid was recrystallized from ethanol to yield yellow crystals of N-(trans-4-Chloro-2-butenyl)phthalimide, wt. 36 g, 61% yield. Analysis calcd. for $C_{12}H_{10}ClNO_2$ (MW 237.25): C, 61.26; H, 4.29; N, 6.02; Cl, 14.94; Found C, 61.18; H, 4.30; N, 5.98; Cl, 14.62.

Ex-7b) Under argon, 3.7 g of sodium metal was dissolved in 200 mL absolute ethanol at 60° C. to 65° C. and then allowed to cool to 30° C. A 27.4 g sample of ethyl acetamidomalonate was then added with good stirring. After 30 minutes, 30 g of Ex-7a was added in 3 portions. The reaction mixture was heated under reflux for 4 h, cooled and filtered. The filtrate was evaporated and the residue was taken in 100 mL of ethylacetate and washed with 100 mL of water. The organic layer was then dried, filtered and concentrated. 100 mL hexane was then added and 27 g of the white solid crude title product was obtained after filtration. This solid Ethyl trans-2-Acetamido-2-carbethoxy-6-phthalimido-4-hexenoate was purified by silica gel column chromatography or recrystallization from ethanol. Analysis calcd. for $C_{21}H_{24}N_2O_7$ (MW 416.15): C, 60.63; H, 5.81; N, 6.77; Found C, 60.51; H, 5.81; N, 6.64.

Ex-7c) A mixture of 25 g ethyl trans-2-acetamido-2-carbethoxy-6-phthalimido-4-hexenoate and 200 mL 37% HCl is heated under reflux for 20 h and then left at 0–2° C. for 20 h. It is then filtered to remove phthalic acid and the filtrate is reduced to dryness in vacuo. 100 mL of absolute ethanol is then added and evaporated under vacuum. Residual solid is taken up in 100 mL absolute ethanol and filtered to give 13 g of trans-2,6-Diamino-4-hexenoic acid dihydrochloride.

Ex-7d) As described in J. Amer. Chem. Soc., Vol.95, 6800, (1973), 10 g trans-2,6-Diamino-4-hexenoic acid dihydrochloride is taken up in 600 mL 95% ethanol and passed through a column of 100 g alumina (Alcoa F-20). The column is eluted with 2 L of 95% ethanol and then eluant is reduced to ~200 ml in vacuo. The precipitate is filtered and dried to give trans-4,5-Dehydrolysine monohydrochloride.

Ex-7e) 11 g of trans-4,5-Dehydrolysine monohydrochloride is dissolved in 10 mL water at 100° C. 7 g copper carbonate is then added in small portions over 30 minutes. The reaction mixture is then cooled to 20° C. and filtered. 1.5 Equivalents of ethyl fluoroacetimidate hydrochloride is then added in portions to above filtrate at 4° C.–5° C. The reaction mixture pH is maintained at ~10.5 throughout the addition with 2N NaOH. After 2 h of stirring, the reaction mixture is passed through ion-exchange resin and eluted with 0.5N aqueous ammonia. The ammonia solution is then carefully acidified to pH 4 with 2N HCl and evaporated to give Example 7.

Example 8

(±)-2-Amino-6-(1-imino-2-fluoroethylamino)-hex-4-ynoic acid hydrochloride

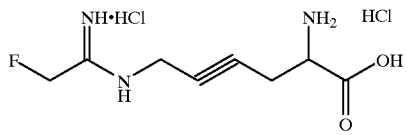

Ex-8a) A mixture of 92.8 g of 1,4-dichloro-2-butyne and 108 g hexamethylenetetramine was refluxed under argon in 500 mL of chloroform for 18 h. The reaction mixture was then cooled and filtered to give 168 g of 1,4-Dichloro-2-butyne hexamethylenetetramine complex as a brown solid.

Ex-8b) The solution of the product of Ex-8a (60 g) in 500 mL absolute ethanol saturated with HCl was refluxed under argon for 18 h and cooled to 20° C. The precipitate formed was filtered and the mother liquor was concentrated to give a yellow waxy solid. This was recrystallized with ether to give 41 g of 1-Amino-4-chloro-2-butyne hydrochloride as an yellow solid.

Analysis calcd. for $C_4H_7Cl_2N$ (MW 141.59): C, 34.78; H, 5.05; N, 10.09; Cl, 50.08; Found C, 31.61; H, 5.70; N, 12.49; Cl, 45.53.

Ex-8c) 14.1 g of 1-Amino-4-chloro-2-butyne hydrochloride was taken up in 70 mL of dioxane and :35 mL water. 4 g NaOH was added and the reaction mixture was stirred for 30 minutes followed by the addition of 21.8 g di-t-butylcarbonate at 20° C. The reaction mixture was stirred at 20° C. to 25° C. for 8 h and then the lower organic layer was separated. The upper aqueous layer was extracted with 100 mL of dichloromethane. Organic layers were combined and washed with 50% aqueous $NaHCO_3$, dried over anhydrous $MgSO_4$, treated with Darco, filtered over celite and concentrated to give a brown oil. This oil was chromatographed to give 9 g of 1-t-Butyloxycarbonylamino-4-chloro-2-butyne as a white solid.

Analysis calcd. for $C_9H_{14}ClNO_2$ (MW 205.25): C, 53.25; H, 6.92; N, 6.96; Cl, 17.27; Found C, 52.67; H, 6.86; N, 6.76; Cl, 17.22.

Ex-8d) 12.1 g 1-t-Butyloxycarbonylamino-4-chloro-2-butyne is refluxed for 16 h with a mixture of 8 g diethyl acetamidomalonate and sodiumethoxide prepared from 900 mg of sodium in 100 mL of absolute ethanol. Ethanol is then removed under vacuum and the residual mass is partitioned between water and ethylacetate/ether (1:1). The organic layer is treated with 0.5N NaOH and 0.5N HCl and washed with water. It is then dried over $Na_2SO_4$, filtered and concentrated. The product is crystallized from ethylacetate/petroleum ether to give ~7 g of Ethyl-2-acetylamino-6-t-butyloxycarbonylamino-2-ethoxycarbonyl-4-hexynoate.

Ex-8e) Following the procedure described in Tetrahedron Lett Vol.21, 4263, (1980) partial saponification of 10.2 g of ethyl-2-acetylamino-6-t-butyloxycarbonylamino-2-ethoxycarbonyl-4-hexynoate is carried out in ethanol with 1.5 equivalent of KOH in water at 20–25° C. for 3 h to give 2-Acetylamino-6-t-butyloxycarbonylamino-2-ethoxycarbonyl-4-hexynoic acid in 90% yield.

Ex-8f) Decarboxylation of 17 g of Ex-8e is done by refluxing in 300 mL dioxane for 24 h. The reaction mixture is then cooled to room temperature and the solvent is removed in vacuum. The residual mass is then taken in 80 mL ethanol and 1.2 equivalents of KOH in water is added for further saponification in 15 h to give 10.5 g of 2-Acetylamino-6-t-butyloxycarbonylamino-4-hexynoic acid.

Ex-8g) 10 g of 2-Acetylamino-6-t-butyloxycarbonylamino-4-hexynoic acid is taken up in 50 mL of acetic acid and 25 mL of 4N HCl in dioxane and stirred for 2 h at 25° C. The reaction mixture is stripped to dryness to give 2-Acetylamino-6-amino-4-hexynoic acid.

Ex-8h) 2.86 g of ethylfluoroacetimidate hydrochloride, 1 equivalent of 2-acetylamino-6-amino-4-hexynoic acid and 6.84 g of DBU are taken up in 200 mL absolute ethanol and stirred for 16 h at 20° C. under argon. Solvent is removed under vacuum and 100 mL water is added. This reaction mixture is filtered through acidic ion exchange column and the product is eluted with 10% pyridine/water. (±)-2-Acetylamino-6-(1-imino-2-fluoroethylamino)-hex-4-ynoic acid hydrochloride is obtained by removing the solvent under vacuum.

Ex-8i) A sample of (±)-2-Acetylamino-6-(1-imino-2-fluoroethylamino)-hex-4-ynoic acid hydrochloride (3 g) is treated with concentrated HCl and then pyridine to afford (±)-2-Amino-6-(1-imino-2-fluoroethylamino)-hex-4-ynoic acid dihydrochloride.

Example 9

1-(1-Imino-2-fluoroethylaminomethyl)-2-(1-carboxylic aminoethyl)cyclopropane dihydrochloride

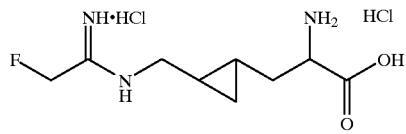

Ex-9a) A solution of 0.05 mol of dimethylsulfonium methylide is generated in situ in DMSO/THF mixture by the reaction of trimethylsulfonium iodide and NaH. Immediately, a solution of 0.05 mol of Ex-7b in 30 mL DMSO is added at 0° C. and the reaction mixture is warmed to 20° C. in 2 h. The reaction mixture is washed with saturated ammonium chloride solution and extracted with ethylacetate. After drying, ethylacetate is evaporated to give Ex-9a.

Ex-9b) The title compound is prepared from Ex-9a similar to the procedure for Ex-7b.

Example 10

2-Amino-5-exomethylene-6-(1-imino-2-fluoroethylamino)-hexanoic acid dihydrochloride

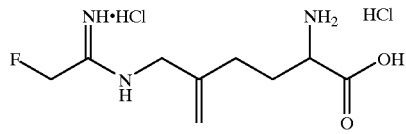

Ex-10a) Ethyl-2-acetamido-2-carbethoxy-5-keto-6-phthalimido hexanoate is prepared as described in *J. Med.*

Chem. 20, 1977, pp 1623–1627 and then is subjected to Wittig reaction with methylenetriphenyl phosphorane to give ethyl-2-acetamido-2-carbethoxy-5-exomethylene-6-phthalimido hexanoate.

Ex-10b) The title compound is prepared from Ex-10a similar to the procedure for Ex-7b.

Example 11

2-Amino-5-cyclopropyl-6-(1-imino-2-fluoroethylamino)-hexanoic acid dihydrochloride

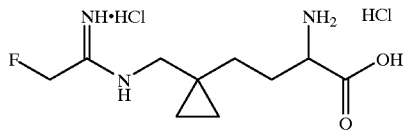

Ex-11a) A sample of Ex-10a is treated with equimolar amount of methylenedimethyl sufurane. After usual work up ethyl-2-acetamido-2-carbethoxy-5-cyclopropyl-6-phthalimido hexanoate is obtained.

Ex-11b) The title compound is prepared from Ex-11a similar to the procedure for Ex-7b.

Example 12

2-Amino-5-methyl-6-(1-imino-2-fluoroethylamino)-hexanoic acid dihydrochloride

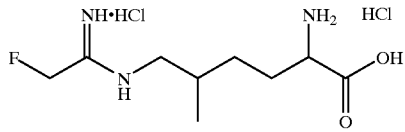

Ex-12a) A sample of 10a is reduced or hydrogenated at 5 position to give ethyl-2-acetamido-2-carbethoxy-5-methyl-6-phthalimido hexanoate.

Ex-12b) The title compound is prepared from Ex-12a similar to the procedure for Ex-7b.

Example 13

2-Amino-4-exomethylene-6-(1-imino-2-fluoroethylamino)-hexanoic acid dihydrochloride

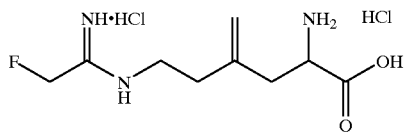

Ex-13a) A sample of 4-oxo-lysine is prepared as described in *J. Chem. Soc. Perkin I*, 1825, (1972). This is subjected to Wittig reaction with methylenetriphenyl phosphorane to give 4-methylene lysine.

Ex-13b) The title compound is prepared from Ex-13a following the procedure as described for the preparation of Ex-7d.

Example 14

N-1-Imino-2-fluoroethyl-4-oxalysine dihydrochloride

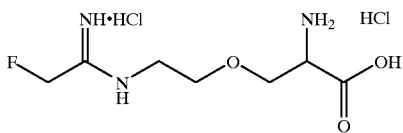

Ex-14a) A sample of O-2-aminoethyl serine or 4-oxalysine dihydrochloride is prepared as described in *Recl. Trav. Chim. Pays-Bas,* 81, 713–719 (1962). It is then converted to the title compound following the procedure as described in Ex-7d.

Example 15

N-1-Imino-2-fluoroethyl-5-oxahomolysine dihydrochloride

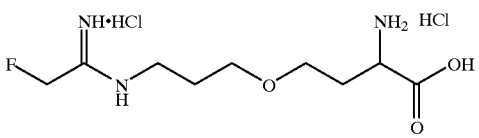

Ex-15a) A sample of 2-amino-4-(2-aminoethoxy)butyric acid is prepared as described in *J. Antibiot.;* 29, 38–43 (1976). It is then converted to the title compound following the procedure as described for the preparation of Ex-7 from Ex-7d.

Example 16

5-fluoro-$N^6$-(1-iminoethyl)-D,L-lysine dihydrochloride

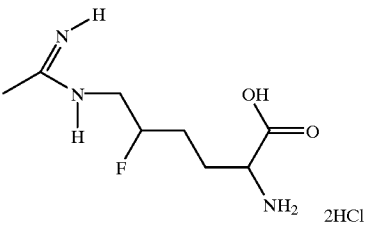

Ex-16a) 5-Fluoro-lysine (45 mg) (Oakwood) was treated in the same manner as described in *J. Antibiotics* 25, 1972, p 179 to form its copper complex. The copper complex of 5-fluoro-lysine was treated with ethyl acetimidate hydrochloride as described in *Analytical Biochemistry* 62, 1974, p 291 to form the epsilon amidine. The copper complex was then broken up as described in *J. Antibiotics* 25, 1972, p 179 to form the title compound. This material was purified via C-18 chromatography to afford 32 mg (46%) of the title compound. C,H,N Calcd. For $C_8H_{16}N_3O_2F$+2.55 HCl+0.20 $NH_4Cl$+0.5 $H_2O$: C, 30.21; H, 6.51; N, 14.00. Found: C, 29.91; H, 6.28; N, 14.01.

Example 17

N-(1-iminoethyl)-2-amino-1,1-difluoroethyl-L-cysteine dihydrochloride

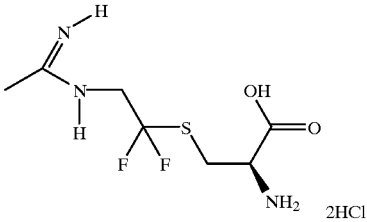

N-Boc-L-cysteine is reacted with 2-chloro-1,1-difluoroethene in the same manner as described in *J. Chem, Res. Miniprint* 12, 1990; p 2868 to form N-Boc-S-(2-chloro-1,1-di fluoroethyl)-L-cysteine. N-Boc-S-(2-chloro-1,1-difluoroethyl)-L-cysteine is reacted with potassium phthalimide in DMF at 100° C. to form the phthalimide. The phthalimide is treated with hydrazine in ethanol to form the amine. The amine is treated with ethyl acetimidate hydrochloride to form the amidine. This material is purified via C-18 chromatography to afford the Boc compound. The Boc group is removed with HCl/dioxane (4 N) in acetic acid to afford the title compound.

Example 18

N-(1-iminoethyl)-2-amino-1,1-difluoroethyl-D,L-homocysteine dihydrochloride

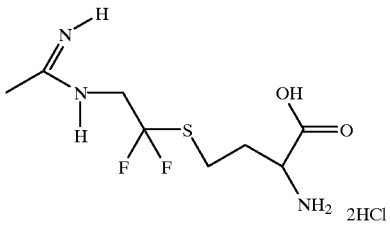

Ex-18a) A solution of N-Boc-D,L-homocysteine (5 mmol) in NaOH (5 mL, 2N) was slowly added to a stirred solution of 1,2-dichloro-1,1-difluoroethane (5 mmol) in DMF. The resulting solution was then warmed to 50° C. for 16 hours. The reaction solution was then poured onto EtOAc and extracted with citric acid (5%) and brine, dried ($Na_2SO_4$) and concentrated in vacuo. The material was purified by flash column chromatography to yield N-Boc-S-(2-chloro-1,1-difluoroethyl)-D,L-homocysteine. Example 18 is prepared in the same manner as described for Example 17 starting with N-Boc-S-(2-chloro-1,1-difluoroethyl)-D,L-homocysteine.

Example 19

N5-(1-iminoethyl)-2,5-diaminopentanoic acid dihydrochloride

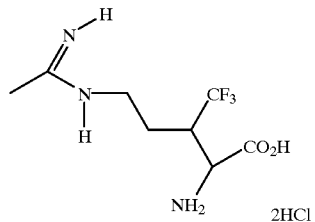

Ex-19a) A solution of diethyl acetamidomalonate (21.7 g, 0.1 mol) was added to a stirred solution sodium ethoxide (4 mmol) in ethanol (50 mL). After addition the resulting solution was cooled to 0° C., followed by the slow addition of 4,4,4-trifluorocrotonitrile (13.3 g, 0.11 mol) over 20 minutes. The reaction solution was then stirred for 1.5 h at RT. The reaction solution was then poured onto EA and extracted with brine, dried $Na_2SO_4$ and concentrated in vacuo to yield a clear liquid that solidified on standing to yield 32.2 g of a white solid.

Ex-19b) The nitrile (11.4 g, 34 mmol) was hydrogenated in ethanol with RaNi at 60 psi at 68° C. for 3 h. The reaction solution was concentrated in vacuo. EtOH and MTBE were added to the oil and the resulting white solid was collected to yield 1.5 g. C,H,N calcd. for $C_{11}H_{15}N_2O_4F_3$; C, 44.45; H, 5.43; N, 9.42. Found C, 44.60; H, 5.18; N, 9.23.

Ex-19c) The lactam (1.0 g, 3.4 mmol) in HCl (conc., 5 mL) was refluxed for 4.5 h. The reaction solution was concentrated in vacuo. The residue was purified via C-18 chromatography to afford the amino acid (500 mg). C,H,N, Cl calcd. for $C_6H_{11}N_2O_2F_3$.2.01 HCl.0.6 $H_2O$; C, 25.35; H, 5.04; N, 9.86; Cl, 25.07. Found C, 25.08; H, 4.97; N, 9.80; Cl, 25.40.

Ex-19d) The amine (0.37 g, 1.3 mmol) was treated with ethyl acetimidate hydrochloride (0.17 g, 1.4 mmol) to form the amidine by the method of Example 3. The material was purified via C-18 chromatography to afford the amidine (98 mg). C,H,N calcd. for $C_8H_{14}N_3O_2F_3$.2.0 HCl.1.5 $H_2O$; C, 28.17; H, 5.61 N, 12.32. Found C, 28.20; H, 5.37; N, 12.23.

Example 20

N6-(2-chloro, 2,2-difluoro-1-iminoethyl)-L-lysine dihydrochloride

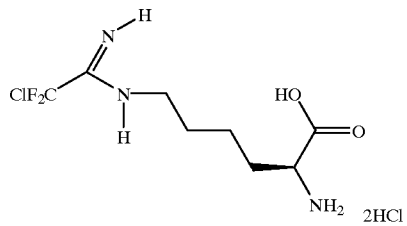

Ex-20a) A three-necked flask was fitted with a dry-ice/acetone condenser and charged with 100 mL of ethanol and 5 g (0.02 mol) of $N^a$-Boc-L-Lys-OH. This was cooled to −78° C. and 5 g (0.045 mol) of chlorodifluoroacetonitrile was added via a gas dispersion tube. After addition was complete, 5 g (0.05 mol) of triethylamine was added. This solution was allowed to stir and warm to 25° C. overnight. Concentration in vacuo afforded a residue which was dissolved in water and placed on a Dowex 50 ion exchange column. The column was washed with water and the product eluted with 10% aqueous pyridine. Removal of the solvent in vacuo afforded 1.26 g of the Boc-protected product as a white solid. Additional purification was carried out on the sample utilizing reverse phase chromatography to afford the Boc-protected product as a white solid.

Mass spectral analysis for $C_{13}H_{22}O_4N_3Cl_1F_2$: M+H=358.

Elemental analysis calcd. for $C_{13}H_{22}O_4N_3Cl_1F_2+H_2O$: C, 36.78; H, 5.14; N, 8.58 Found: C, 36.39; H, 5.38; N, 8.3

Ex-20b) To a flask containing 0.185 g of the product of example Ex-20a was added 20 mnL of 2N HCl. This mixture was stirred for 2½ hours, diluted with water and lyophilized to afford the title compound as a colorless oil. $^1$H-NMR ($D_2O$) 1.2–1.5 (m, 2H), 1.5–1.7 (m, 2H), 1.7–2.0 (m, 2H), 3.35 (t, 2H), 3.9 (t, 1H);

Elemental anal. calcd. for $C_8H_{16}O_2N_3Cl_3F_2+4\ H_2O+0.15$ lysine: C, 24.75; H, 6.14; N, 10.67 Found: C, 24.96; H, 6.26; N, 10.39

Example 21

$N^6$-(2-fluoro-1-iminoethyl)-L-lysine dihydrochloride

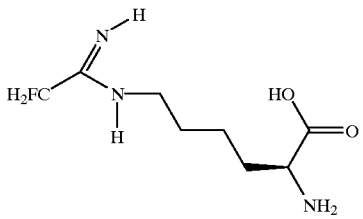

Ex-21a) To a solution of 5 g (0.18 mol) of Na-Cbz-lysine in 50 mL of ethanol was added 3.8 g (0.027 mol) of ethyl fluoroacetimidate. This was stirred at 25° C. for 24 hours. Concentrated reaction mixture to give an oily residue. Chromatography (C 18, acetonitrile/water) eluted two fractions containing the Cbz-protected title product. The first fraction containing 1.5 g of a 2:1 ratio of Cbz-protected product to starting Cbz-lysine and a second fraction containing 0.4 g of Cbz-protected product.

$^1$H-NMR($D_2O$) 1.2–1.4 (m, 2H), 1.6–1.7 (m, 3H), 1.7–1.8 (m, 1H), 3.2 (t, 2H), 4.1 (t, 1H), 5.0 (s, 2H), 5.1 (d, 2H), 7.3 (s, 5H);

Elemental analysis calcd. for $C_{16}H_{22}O_4N_3F_1+CF_3CO_2H+2.5H_2O$: C, 43.38; H, 5.66; N, 8.43 Found: C, 43.65; H, 5.30; N, 8.25

Ex-21b) A solution of 1.5 g of the first fraction product of Ex-21a in 20 mL of 2 N HCl was stirred at reflux for 2½ hours. Removed heat and concentrated in vacuo to afford 0.5 g of the title product as a colorless oil.

$^1$H-NMR($D_2O$) 1.3–1.5 (m, 2H), 1.5–1.7 (m, 2H), 1.7–2.0 (m, 2H), 3.25 (t, 2H), 3.95 (t, 1H), 5.15 (d, 2H);

Elemental analysis calcd. for $C_8H_{18}O_2N_3F_1Cl_2+5H_2O+0.5$ lysine: C, 27.65; H, 7.59; N, 11.73 Found: C, 27.74; H, 7.15; N, 11.56

Example 22

5-fluoro-$N^6$-(1-(thiophene-2-yl)-1-iminomethyl) D, L-lysine

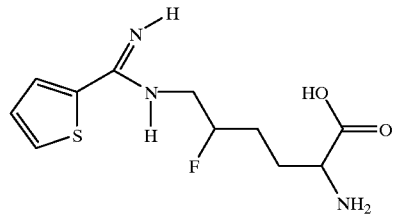

Ex-22a) To a mixture of 2-cyanothiophene and 1 equivalent of ethanol is bubbled anhydrous HCl gas to afford the ethyl imidate.

Ex-22b) The product of Ex-22a is added to a solution of 5-fluorolysine in ethanol and allowed to stir until reaction is complete. Purification with chromatography afford the title product.

Example 23

N-(2-fluoro-1-iminoethyl)-3-aminopropyl-L-cysteine dihydrochloride

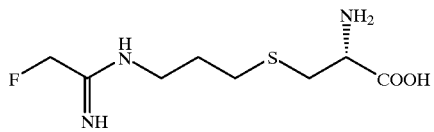

Ex-23a) 2.5 g (5 mmol) S-($N^w$-Boc-3-aminoethyl)-$N^a$-Fmoc-L-cysteine was dissolved in 25 mL dichloromethane and deprotected by the addition of 8 mL trifluoroacetic acid with 25 minutes stirring at room temperature. The solvent was evaporated in vacuo to afford S-(3-aminoethyl)-$N^a$-Fmoc-L-cysteine.

Ex-23b) The product of Ex-23a was allowed to react with 1.05 g (10 mmol) ethyl fluoroacetimidate hydrochloride in 40 mL ethanol in the presence of 2.6 mL (15 mmol) diisopropylethylamine (DIPEA) with stirring for 18 hours at room temperature. The Fmoc-protected product was isolated on preparative reversed phase HPLC using a gradient of acetonitrile in H2O containing 0.05% TFA (10–50% AcN in 30 minutes). Yield 1.2 g (2.6 mmol; 52%) white solid material.

FAB MS: M+H=460

Ex-23c) 1.2 g (2.6 mmol)of the product of from Ex-23b was deprotected in a mixture of 5 mL diethylamine and 20 mL DMF with stirring for 15 minutes. The solvent was evaporated under reduced pressure and the remaining oil was purified on preparative reversed phase HPLC using a gradient of acetonitrile in $H_2O$ containing 0.05% TFA (0–30% AcN in 30 minutes) to yield 0.426 mg (0.93 mmol; 36%) of the title product.

FAB MS: M+H=238

$^1$H NMR ($D_2O$): 1.77–1.92 (m; 2H), 2.49–2.61 (m; 2H), 2.86–3.05 (m; 4H), 3.38–3.48 (m; 2H), 4.02–4.08 (m; 1H), 5.04–5.10 s; 1H) and 5.19–5.25 (s; 1H).

Example 24

N-(2-fluoro-1-iminoethyl)-2-aminoethyl-L-cysteine dihydrochloride

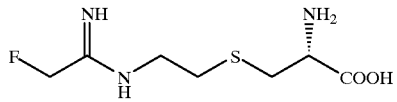

Ex-24a) 20 g (50 mmol) S-(N$^w$-Z-2-aminoethyl)-N$^a$-Boc-L-cysteine (oil) was dissolved in 100 mL methanol and the Z-group was removed in the presence of 5 g NH$_4$OOCH and 1 g Pd black with stirring for 24 hours under N2. The product was isolated on preparative reversed phase HPLC using a gradient of acetonitrile in H$_2$O containing 0.05% TFA (0–40% AcN in 30 minutes)to yield 5.6 g (42%) of S-(2-aminoethyl)-N-Boc-L-cysteine.

FAB MS: M+H=265

Ex-24b) 1.4 g (5.3 mmol) of the product of Ex-24a was dissolved in 25 mL ethanol and allowed to react with 1.05 g (10 mmol) of ethyl fluoroacetimidate hydrochloride in the presence of 2.6 mL (15 mmol) DIPEA with stirring for 18 hours at room temperature. The solvent was evaporated under reduced pressure and the remaining oil was purified on preparative reversed phase HPLC using a gradient of acetonitrile in H$_2$O containing 0.05% TFA (10–50% AcN in 30 minutes) to yield 0.95 g (2.94 mmol; 55%) of the Boc-protected product.

FAB MS: M+H=324

Ex-24c) 0.95 g (2.94 mmol) of the product of Ex-24b was dissolved in 25 mL 1 N HCl and stirred for 12 hours at room temperature. This was diluted with 200 mL H$_2$O and lyophilized to yield 0.46 g (1.55 mmol; 53%) of the title product as an oil.

FAB MS: M+H=224

$^1$H NMR (D$_2$O): 2.71–2.85 (m; 2H), 2.96–3.18 (m; 2H), 3.42–3.56 (m; 2H), 4.18–4.28 (m; 1H), 5.18–5.22 (s; 1H) and 5.25–5.30 (s; 1H).

Example 25

N-(2-fluoro-1-iminoethyl)-2-aminoethyl-D,L-homocysteine dihydrochloride

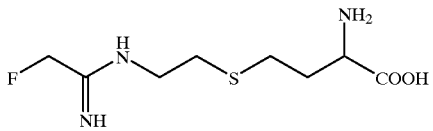

Ex-25a) 4.7 g (20 mmol) N$^a$-Boc-homocysteine was dissolved in 50 mL DMF and 1.6 g (40 mmol) NaH (60% dispersion in mineral oil) was added to the solution. After 15 minutes stirring at room temperature 4.1 g (20 mmol) 2-bromoethylamine hydrobromide was added to the mixture slowly. Stirring was continued for 16 hours at room temperature. DMF was removed under reduced pressure and the residue was isolated on preparative reversed phase HPLC using a gradient of acetonitrile in H$_2$O containing 0.05% TFA (0–40% AcN in 30 minutes) to yield 4.05 g (10.3 mmol; 52%) of the S-(aminoethyl)-N-Boc-L-cysteine as an oil.

FAB MS: M+H=279

$^1$H NMR (D$_2$O): 1.25–1.35 (m; 9H), 1.78–2.10 (m;2H), 2.44–2.67 (m;2H), 2.69–2.80 (m; 2H), 3.04–3.15 (m; 2H) and 4.06–4.22 (m; 1H).

Ex-25b) 1.5 g (3.8 mmol)of the product of example Ex-25a was dissolved in 20 mL ethanol and reacted with 0.63 g (6 mmol) ethyl-fluoroacetimidate hydrochloride in the presence of 1.05 mL (6 mmol) DIPEA with stirring for 18 hours at room temperature. The solvent was evaporated under reduced pressure and the remaining oil was purified on preparative reversed phase HPLC using a gradient of acetonitrile in H$_2$O containing 0.05% TFA (0–40% AcN in 30 minutes) to yield 1.4 g (3.1 mmol; 82%)of the Boc-protected product as an oil.

FAB MS: M+H=338

$^1$H NMR (D$_2$O): 1.24–1.34 (m; 9H), 1.75–2.12 (m; 2H), 2.43–2.83 (m; 4H), 3.41–3.55 (t; 2H), 4.04–4.22 (m; 1H), 5.08–5.14 (s; 1H) and 5.23–5.28 (s; 1H).

Ex-25c) 1.4 g (3.1 mmol) of the product of example Ex-25b was dissolved in 25 mL 1 N HCl and stirred for 12 hours at room temperature. This was diluted with 300 mL H$_2$O and lyophilized to yield 0.91 g (2.93 mmol; 95%) of the title product as an oil.

FAB MS: M+H=238

$^1$H NMR (D$_2$O): 1.98–2.25 (m; 2H), 2.60–2.84 (m; 4H), 3.43–3.56 (m; 2H), 4.06–4.16 (t; 1H), 5.08–5.14 (s; 1H) and 5.23–5.28 (s; 1H).

Example 26

N-(2-fluoro-1-iminoethyl)-2-aminoethyl-L-homocysteine dihydrochloride

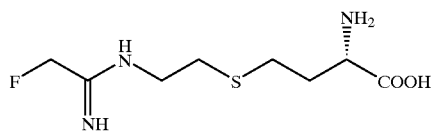

Ex-26a) The title product was prepare as in Example 25 utilizing N$^a$-Boc-L-homocysteine to afford 7.5 g (24.2 mmol; 96%) of the title product as an oil.

FAB MS; M+H=2:38

$^1$H NMR (D$_2$O): 1.98–2.25 (m; 2H), 2.60–2.84 (m; 4H), 3.43–3.56 (m; 2H), 4.06–4.16 (t; 1H), 5.08–5.14 (s; 1H) and 5.23–5.28 (s; 1H).

Example 27

N-(2-chloro-2,2-difluoro-1-iminoethyl)-3-aminoethyl-D,L-homocysteine dihydrochloride

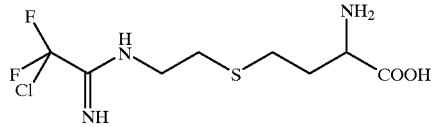

Ex-27a) 2.8 g (10 mmol) of the product of Ex-25a was dissolved in 40 mL ethanol and 1.75 mL (10 mmol) DIPEA was added to the solution. In ice bath difluoro-chloroacetonitrile (F$_2$ClCN) gas was bubbled into the mixture for 10 minutes. It was stirred for 24 hours at room temperature and then the solvent was evaporated in vacuo. The remaining oil is purified on preparative reversed phase HPLC using a gradient of acetonitrile in H,O containing 0.05% TFA (5–40% AcN in 30 minutes) to yield 2.4 g (6.2 mmol; 62%)of the Boc-protected product as an oil.

FAB MS: M+H=390

Ex-27b) 2.4 g (6.2 mmol) the product of Ex-27a is dissolved in 50 mL 1 N HCl and stirred for 12 hours at room temperature. This is diluted with 200 mL H$_2$O and lyophilized to yield 1.4 g (4.8 mmol; 77%) of the title product as an oil.

FAB MS: M+H=290

Example 28

N-(2,2-difluoro-1-iminoethyl)-2-aminoethyl-D,L-homocysteine dihydrochloride

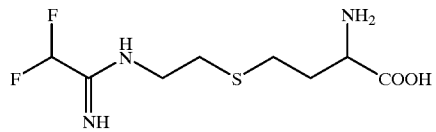

Ex-28a) 2.4 g (6.2 mmol) of the product of Ex-27a was dissolved in 50 mL MeOH and it was treated with 1 g of H$_4$NOOCH and 0.2 g of Pd black with stirring under N$_2$ for 48 hours. The catalyst was filtered off and the Boc-protected product was purified on preparative reversed phase HPLC using a gradient of acetonitrile in H$_2$O containing 0.05% TFA (10–50% AcN in 30 minutes) to yield 1.06 g of a white solid (2.26 mmol; 23% overall).

FAB MS: M+H=356

Ex-28b) 1.06 g (2.26 mmol) of the product of Ex-28a was dissolved in 20 mL 1 N HCl and stirred for 12 hours at room temperature. This was diluted with 200 mL H$_2$O and lyophilized twice to yield 0.69 g (2.1 mmol; 96%) of the title product as an oil.

FAB MS: M+H=256

$^1$H NMR (D$_2$O): 2.02–2.28 (m; 2H), 2.55–2.90 (m; 4H), 3.48–3.65 (m; 2H), 4.03–4.18 (m; 1H) and 6.40–6.80 (t; 1H).

Example 29

N-(2-fluoro-1-iminoethyl)-3-aminopropyl-D,L-homocysteine dihydrochloride

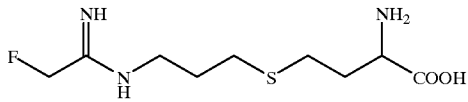

Ex-29a) N$^\alpha$-Boc-homocysteine is dissolved in DMF and NaH (60% dispersion in mineral oil) is added to the solution. After 15 minutes stirring at room temperature 2-bromopropylamine hydrobromide is added to the mixture slowly. Stirring is continued for 16 hours at room temperature. DMF is removed under reduced pressure and the residue is isolated on preparative reversed phase HPLC using a gradient of acetonitrile in H$_2$O containing 0.05% TFA to afford S-(aminopropyl)-N$^\alpha$-Boc-Homocysteine.

Ex-29b) The product of Ex-29a is dissolved in 20 mL ethanol and reacted with ethyl-fluoroacetimidate hydrochloride in the presence of DIPEA with stirring for 18 hours at room temperature. The solvent is evaporated under reduced pressure and the remaining oil is purified on preparative reversed phase HPLC using a gradient of acetonitrile in H$_2$O containing 0.05% TFA to afford the Boc-protected product.

Ex-29c) The product of Ex-29b is dissolved in 1 N HCl and stirred for 12 hours at room temperature. This is diluted with H$_2$O and lyophilized to afford the title product.

Example 30

N-(2-fluoro-1-iminoethyl)-2-aminoethyl-D,L-bishomocysteine dihydrochloride

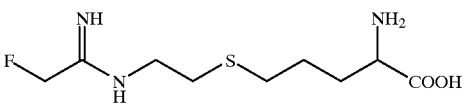

Ex-30a) N$^\alpha$-Cbz-glutamic acid, a-benzyl ester is dissolved in THF and treated with Borane. Isolation affords the protected glutamic alcohol.

Ex-30b) The product of Ex-30a is treated with triphenyl phosphine and carbon tetrabromide. Isolation affords 2-Cbz-amino, 5-bromopentanoic acid benzyl ester.

Ex-30c) The product of Ex-30b is dissolved in THF and allowed to react with sodium hydride followed by 2-Boc-amino mercaptoethane. Isolation affords the S-(Boc-aminoethyl)-N$^\alpha$-Cbz-Bishomocysteine benzyl ester.

Ex-30d) The product of Ex-30c is Boc-deprotected with HCl to afford S-(aminoethyl)-N$^\alpha$-Cbz-Bishomocysteine benzyl ester.

Ex-30e) The product of Ex-30d is allowed to react with ethyl fluoroacetimidate hydrochloride as in Ex-25b to afford the Cbz-protected product as a benzyl ester.

Ex-30f) Deprotection of the product of Ex-30e via hydrogenation affords the title product.

Example 31

2-[N-(2-fluoro-1-iminoethyl)-aminomethyl]-5-[2(S)-aminopropionic acid-3-yl]-thiophene dihydrochloride

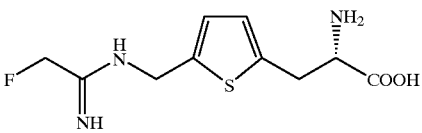

Ex-31a) 2-Bromothiophene-5-carboxamide is allowed to react with N-acetyl dehydroalanine methyl ester under Heck coupling conditions to afford 2-(2-(acetylamino)propenoic methyl ester-3-yl)thiophene-5-carboxamide.

Ex-31b) The product of Ex-31a is subjected to chiral hydrogenation conditions to afford 2-(2(S)-(acetylamino) propenoic methyl ester-3-yl)thiophene-5-carboxamide.

Ex-31c) The product of Ex-31b is subjected to mild saponification to afford 2-(2(S)-(acetylamino)propanoic acid-3-yl)thiophene-5-carboxamide.

Ex-31d) The product of Ex-31c is allowed to react with LiBEt$_3$H to afford 2-2(S)-(acetylamino)propanoic acid-3-yl)thiophene-5-aminomethyl.

Ex-31e) The product of Ex-31d is allowed to react with ethyl fluoroacetimidate hydrochloride as in example Ex-24b to afford the Acetyl-protected product.

Ex-31f) Deprotection of the product of Ex-31e via hydrolysis affords the title product.

Example 32

N[6]-(2-chloro-1-iminoethyl)-L-lysine dihydrochloride

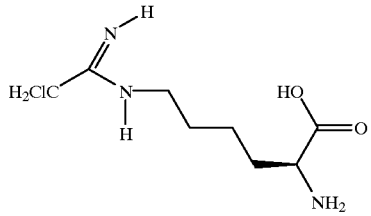

Ex-32) The method of Example 20 was utilized to prepare the title product.

Mass spectral analysis for $C_8H_{16}N_3O_2Cl_1$: M+H=222.

BIOLOGICAL DATA

The activity of the above listed compounds as NO synthase inhibitors has or can be determined in the following assays:

Citrulline Assay for Nitric Oxide Synthase

Nitric oxide synthase activity is measured by monitoring the conversion of [3H]-arginine to [3H]-citrulline. Mouse inducible nitric oxide synthase (miNOS) was prepared from an extract of LPS-treated RAW 264.7 cells and partially purified by DEAE-Sepharose chromatography. Rat brain constitutive nitric oxide synthase (mNOS) was prepared from an extract of rat cerebellum and partially purified by DEAE-Sepharose chromatography. Enzyme and inhibitors were incubated at 37° C. for 15 minutes in a reaction volume of 100 mL with the following components added to start the reaction: 50 mM Tris (pH 7.6), 1 mg/ml bovine serum albumin, 1 mM DTT, 2 mM $CaCl_2$, 10 mM FAD, 10 mM tetrahydrobiopterin, 30 mM L-arginine containing L-[2,3-3H]-arginine at 300 cpm/pmole and 1 mM NADPH. For constitutive NOS, 50 nM calmodulin was also added. The reaction was terminated by addition of cold stop buffer containing 10 mM EGTA, 100 mM HEPES, pH 5.5 and 1 mM citrulline. [3H]-Citrulline was separated by chromatography on Dowex 50W X-8 cation exchange resin and radioactivity determined with a liquid scintillation counter.

Raw Cell Nitrite Assay

RAW 264. 7 cells are plated to confluency on a 96-well tissue culture plate grown overnight (17 h) in the presence of LPS to induce NOS. A row of 3–6 wells were left untreated and served as controls for subtraction of nonspecific background. The media was removed from each well and the cells are washed twice with Krebs-Ringers-Hepes (25 mM, pH 7.4) with 2 mg/ml glucose. The cells are then placed on ice and incubated with 50 mL of buffer containing L-arginine (30 mM) +/-inhibitors for 1 h. The assay is initiated by warming the plate to 37° C. in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. T. P. Misko et al, *Analytical Biochemistry*, 214, 11–16 (1993). All values are the average of triplicate wells and are compared to a background-subtracted induced set of cells (100% value).

In Vivo Assay

Rats are treated with an intraperitoneal injection of 10 mg/kg of endotoxin (LPS) with or without oral administration of the nitric oxice synthase inhibitors. Plasma nitrites were measured 5 hours post-treatment. The results show that the administration of the nitric oxide synthase inhibitor decreases the rise in plasma nitrites, a reliable indicator of the production of nitric oxide, induced by endotoxin.

IP is the abbreviation for 2-iminopiperidine
LPS is the abbreviation for endotoxin From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula (I):

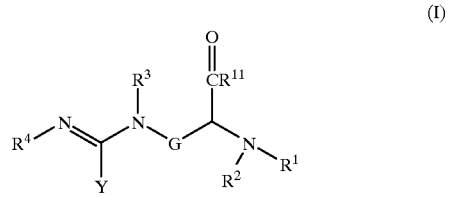

or a pharmaceutically acceptable salt thereof, wherein:

$R^1$ is selected from the group consisting of H, $C_1$–$C_{10}$ alkyl, $C_2$–$C_{10}$ alkenyl, and $C_2$–$C_{10}$ alkynyl;

$R^2$ is selected from the group consisting of H, $C_1$–$C_{10}$ alkyl, $C_2$–$C_{10}$ alkenyl, $C_2$–$C_{10}$ alkynyl, and either R or S alpha-amino acid;

$R^3$ and $R^4$ are independently selected from the group consisting of H, $C_1$–$C_{10}$ alkyl, $C_2$–$C_{10}$ alkenyl, $C_2$–$C_{10}$ alkynyl, and $NO_2$;

wherein $R^1$, $R^2$, $R^3$ and $R^4$ are optionally substituted from the group consisting of lower alkyl, lower alkenyl, lower alkynyl, cycloalkyl, aryl, hydroxy, lower alkoxy, aryloxy, thiol, lower thioalkoxy, halogen, cyano, nitro, amino, carboxy, carboxyalkyl, carboxyaryl, amidino, and guanidino;

$R^{11}$ is selected from the group consisting of hydroxyl and R or S alpha-amino acid;

G is selected from the group consisting of $C_1$–$C_{10}$ alkylene, $C_2$–$C_{10}$ alkenediyl, and $C_2$–$C_{10}$ alkanediyl, each of which is optionally substituted with one or more selected from the group consisting of halogen, hydroxy, trifluoromethyl, nitro, cyano, amino, $C_1$–$C_{10}$ alkyl, $=CH_2$, $C_2$–$C_{10}$ alkenyl, $C_2$–$C_{10}$ alkynyl, and $C_1$–$C_{10}$ alkoxy, each of which are optionally substituted from the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

G is selected from the formula $-(CH_2)_p-(CX^1X^2)_r-(CH_2)_s-Q-(CH_2)_t-(CX^3X^4)_u-(CH_2)_v$ where p, r, s, t, u, v are independently 0 to 3 and Q is oxygen, $C=O$, $S(O)_a$ wherein a is 0 to 2, with the proviso that when a is 1 or 2, G must contain halogen, or $NR^{12}$ wherein $R^{12}$ is selected from the group consisting of H and $C_1$–$C_{10}$ alkyl which are optionally substituted with one or more selected from the group consisting of $C_1$–$C_{10}$ alkyl, $C_1$–$C_{10}$ alkoxy, hydroxy, trifluoromethyl, nitro, cyano, amino, and halogen;

G is selected from the formula $-(CH_2)_w-(CX^5X^6)_y-(CH_2)_z-A-(CH_2)_k-(CX^7X^8)_j-(CH_2)_h$ wherein w, y, z, k, j, h are independently 0 to 3 and A is a 3 to 6 membered carbocyclic radical which are optionally substituted with one or more selected from the group consisting of halogen, $C_1$–$C_{10}$ alkyl, $C_1$–$C_{10}$ alkoxy, hydroxy, trifluoromethyl, nitro, cyano, and amino, each of which are optionally substituted with halogen or $C_1$–$C_{10}$ alkyl, with the proviso that when G is selected from the formula —(CH$_2$)$_w$—(CX$^5$X$^6$)$_y$—(CH$_2$)$_z$—A—(CH$_2$)$_k$—(CX$^7$X$^8$)$_j$—(CH$_2$)$_h$, Y must contain halogen;

$X^1$, $X^2$, $X^3$, $X^4$, $X^5$, $X^6$, $X^7$, $X^8$ are independently not present, H, halogen, $C_1$–$C_{10}$ alkyl, =CH$_2$, $C_2$–$C_{10}$ alkenyl, or $C_2$–$C_{10}$ alkynyl, wherein $C_1$–$C_{10}$ alkyl, =CH$_2$, $C_2$–$C_{10}$ alkenyl, and $C_2$–$C_{10}$ alkynyl which is optionally substituted from one or more of the group consisting of lower alkyl, lower alkenyl, lower alkynyl, cycloalkyl, heterocyclyl, aryl, heteroaryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro;

Y is selected from the group consisting of, $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl, each of which is optionally substituted with one or more selected from the group consisting of halogen, hydroxy, trifluoromethyl, nitro, cyano, amino, $C_1$–$C_{10}$ alkyl, $C_2$–$C_{10}$ alkenyl, $C_2$–$C_{10}$ alkynyl, and $C_1$–$C_{10}$ alkoxy; or Y is NR$^9$R$^{10}$ wherein R$^9$ and R$^{10}$ are independently selected from the group consisting of H, $C_1$–$C_{10}$ alkyl, $C_3$–$C_{10}$ cycloalkyl, $C_2$–$C_{10}$ alkenyl, $C_2$–$C_{10}$ alkynyl, nitro, amino, aryl, and $C_1$–$C_{10}$ alkaryl;

with the proviso that at least one of G or Y contains a halogen.

2. A compound as claimed in claim 1 wherein:

G is selected from the group consisting of $C_1$–$C_{10}$ alkylene, $C_2$–$C_{10}$ alkenediyl, and $C_2$–$C_{10}$ alkanediyl, each of which is optionally substituted with one or more selected from the group consisting of halogen, hydroxy, trifluoromethyl, nitro, cyano, amino, $C_1$–$C_{10}$ alkyl, =CH$_2$, $C_2$–$C_{10}$ alkenyl, $C_2$–$C_{10}$ alkynyl, and $C_1$–$C_{10}$ alkoxy, each of which is optionally substituted from the group consisting of lower alkyl, lower alkenyl, lower alkynyl, cycloalkyl, aryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro; or G is selected from the formula (CH$_2$)$_p$—(CX$^1$X$^2$)$_r$—(CH$_2$)$_s$—Q—(CH$_2$)$_t$—(CX$^3$X$^4$)$_u$—(CH$_2$)$_v$ where p, r, s, t, u, v are independently 0–3 and Q is oxygen, C=O, S(O)$_a$ wherein a is 0 to 2, with the proviso that when a is 1 or 2, G must contain a halogen, or NR$^{12}$ where R$^{12}$ is selected from the group consisting of H and $C_1$–$C_{10}$ alkyl, which is optionally substituted with one or more selected from the group consisting of $C_1$–$C_{10}$ alkyl, $C_1$–$C_{10}$ alkoxy, hydroxy, trifluoromethyl, nitro, cyano, amino, and halogen.

3. A compound as claimed in claim 2 wherein:

G is selected from the group consisting of $C_1$–$C_{10}$ alkylene, $C_2$–$C_{10}$ alkenediyl, and $C_2$–$C_{10}$ alkanediyl, each of which is optionally substituted with one or more selected from the group consisting of halogen, hydroxy, trifluoromethyl, nitro, cyano, amino, $C_1$–$C_{10}$ alkyl, =CH$_2$, $C_2$–$C_{10}$ alkenyl, $C_2$–$C_{10}$ alkynyl, and $C_1$–$C_{10}$ alkoxy, each of which is optionally substituted from the group consisting of lower alkyl, lower alkenyl, lower alkynyl, cycloalkyl, aryl, hydroxy, lower alkoxy, aryloxy, thiol, lower thioalkoxy, halogen, cyano, nitro, amino, carboxy, carboxyalkyl, carboxyaryl, amidino, guanidino, trifluoromethyl, and nitro; and Y is selected from the group consisting of $C_1$–$C_{10}$ haloalkyl, $C_1$–$C_{10}$ dihaloalkyl, $C_1$–$C_{10}$ trihaloalkyl, $C_1$–$C_{10}$ alkyl, $C_3$–$C_{10}$ cycloalkyl, $C_2$–$C_{10}$ alkenyl, and $C_2$–$C_{10}$ alkynyl each of which is optionally substituted with one or more selected from the group consisting of halogen, hydroxy, trifluoromethyl, nitro, cyano, amino, $C_1$–$C_{10}$ alkyl, $C_2$–$C_{10}$ alkenyl, $C_2$–$C_{10}$ alkynyl, and $C_1$–$C_{10}$ alkoxy.

4. A compound as claimed in claim 3 wherein:

R$^1$ and R$^2$ are H,

R$^3$ and R$^4$ are independently selected from the group consisting of H and NO$_2$;

G is selected from the group consisting of $C_1$–$C_{10}$ alkylene, $C_2$–$C_{10}$ alkenediyl, and $C_2$–$C_{10}$ alkanediyl, each of which is optionally substituted with one or more selected from the group consisting of halogen, hydroxy, trifluoromethyl, nitro, cyano, amino, $C_1$–$C_{10}$ alkyl, =CH$_2$, $C_2$–$C_{10}$ alkenyl, $C_2$–$C_{10}$ alkynyl, and $C_1$–$C_{10}$ alkoxy, each of which is optionally substituted from the group consisting of lower alkyl, lower alkenyl, lower alkynyl, cycloalkyl, aryl, hydroxy, lower alkoxy, thiol, lower thioalkoxy, halogen, cyano, nitro, amino, carboxy, carboxyalkyl, carboxyaryl, amidino, guanidino, trifluoromethyl, and nitro; and Y is selected from the group consisting of $C_1$–$C_6$ alkyl, $C_3$–$C_6$ cycloalkyl, $C_2$–$C_6$ alkenyl, and $C_2$–$C_6$ alkynyl, each of which is optionally substituted with one or more halogens, or NHR$^9$ wherein R$^9$ is selected from the group consisting of H, $C_1$1 $C_6$ alkyl $C_3$–$C_6$ cycloalkyl, $C_2$–$C_6$ alkenyl, and $C_2$–$C_6$ alkynyl.

5. A compound as claimed in claim 4 wherein:

R$^1$, R$^2$, R$^3$ and R$^4$ are each H;

G is $C_1$–$C_5$ alkylene substituted with at least one halogen; and

Y is $C_1$–$C_6$ alkyl.

6. A compound as claimed in claim 1 wherein:

R$^1$, R$^2$, R$^3$ and R$^4$ are each H;

Y is $C_1$–$C_{10}$ haloalkyl or $C_1$–$C_{10}$ alkyl; and

G is selected from the formula (CH$_2$)$_p$—(CX$^1$X$^2$)$_r$—(CH$_2$)$_s$—Q—(CH$_2$)$_t$—(CX$^3$X$^4$)$_u$—(CH$_2$)$_v$ where p, r, s, t, u, v are independently 0–3 and Q is oxygen, C=O, S(O)$_a$ wherein a is 0 to 2, with the proviso that when a is 1 or 2, G must contain a halogen, or NR$^{12}$ where R$^{12}$ is selected from the group consisting of H and $C_1$–$C_{10}$ alkyl, which is optionally substituted with one or more selected from the group consisting of $C_1$–$C_{10}$ alkyl, $C_1$–$C_{10}$ alkoxy, hydroxy, trifluoromethyl, nitro, cyano, amino, and halogen.

7. A compound selected from the group consisting of:

4,4-difluoro-N$^5$-(1-iminoethyl)-L-ornithine dihydrochloride;

4,4-difluoro-N$^6$-(1-iminoethyl)-L-lysine dihydrochloride;

5,5-difluoro-N$^6$-(1-iminoethyl)-L-lysine dihydrochloride;

N$^6$-(2,2,2-trifluoro-1-iminoethyl)-L-lysine dihydrochloride;

N$^6$-(2,2,2-trichloro-1-iminoethyl)-L-lysine dihydrochloride;

N$^6$-(2,2-difluoro-1-iminoethyl)-L-lysine dihydrochloride;

(±)-E-2-Amino-6-(1-imino-2-fluoroethylamino)-hex-4-enoic acid dihydrochloride;

(±)-2-Amino-6-(1-imino-2-fluoroethylamino)-hex-4-ynoic acid hydrochloride;

1-(1-Imino-2-fluoroethylaminomethyl)-2-(1-carboxylic aminoethy)cyclopropane dihydrochloride;

2-Amino-5-exomethylene-6-(1-imino-2-fluoroethylamino)-hexanoic acid dihydrochloride;

2-Amino-5-cyclopropyl-6-(1-imino-2-fluoroethylamino)-hexanoic acid dihydrochloride;

2-Amino-5-methyl-6-(1-imino-2-fluoroethylamino)-hexanoic acid dihydrochloride;

2-Amino-4-exomethylene-6-(1-imino-2-fluoroethylamino)-hexanoic acid dihydrochloride;

N-1-Imino-2-fluoroethyl-4-oxalysine dihydrochloride;

N-1-Imino-2-fluoroethyl-5-oxahomolysine dihydrochloride;

5-fluoro-$N^6$-(1-iminoethyl)-D,L-lysine dihydrochloride;

N-(1-iminoethyl)-2-amino-1,1-difluoroethyl-L-cysteine dihydrochloride;

N-(1-iminoethyl)-2-amino-1,1-difluoroethyl-D,L-homocysteine dihydrochloride;

N5-(1-iminoethyl)-2,5-diaminopentanoic acid dihydrochloride;

$N^6$-(2-chloro, 2,2-difluoro-1-iminoethyl)-L-lysine dihydrochloride;

$N^6$-(2-fluoro-1-iminoethyl)-L-lysine dihydrochloride;

N-(2-fluoro-1-iminoethyl)-3-aminopropyl-L-cysteine dihydrochloride;

N-(2-fluoro-1-iminoethyl)-2-aminoethyl-L-cysteine dihydrochloride;

N-(2-fluoro-1-iminoethyl)-2-aminoethyl-D,L-homocysteine dihydrochloride;

N-(2-fluoro-1-iminoethyl)-2-aminoethyl-L-homocysteine dihydrochloride;

N-(2-chloro-2,2-difluoro-1-iminoethyl)-3-aminoethyl-D,L-homocysteine dihydrochloride;

N-(2,2-difluoro-1-iminoethyl)-2-aminoethyl-D,L-homocysteine dihydrochloride;

N-(2-fluoro-1-iminoethyl)-3-aminopropyl-D,L-homocysteine dihydrochloride;

N-(2-fluoro-1-iminoethyl)-2-aminoethyl-D,L-bishomocysteine dihydrochloride; and $N^6$-(2-chloro-1-iminoethyl)-L-lysine dihydrochloride.

8. A compound of claim 7 selected from the group consisting of:

N-(2-fluoro-1-iminoethyl)-3-aminopropyl-L-cysteine dihydrochloride;

N-(2-fluoro-1-iminoethyl)-2-aminoethyl-L-cysteine dihydrochloride;

N-(2-fluoro-1-iminoethyl)-2-aminoethyl-D,L-homocysteine dihydrochloride; and

N-(2-fluoro-1-iminoethyl)-2-aminoethyl-L-homocysteine dihydrochloride.

9. A method of inhibiting nitric oxide synthesis in a subject in need of such inhibition by administering a therapeutically effective amount of a compound of claims 1, 2, 3, 4, 5, 6, 7 or 8.

10. A method of selectively inhibiting nitric oxide produced by inducible NO synthase over nitric oxide produced by the constitutive forms of NO synthase in a subject in need of such selective inhibition by administering a therapeutically effective amount of a compound of claim 1, 2, 3, 4, 5, 6, 7 or 8.

11. A method of lowering nitric oxide levels in a subject in need of such by administering a therapeutically effective amount of a compound of claims 1, 2, 3, 4, 5, 6, 7 or 8.

12. A pharmaceutical composition comprising a compound of claims 1, 2, 3, 4, 5, 6, 7 or 8 together with one or more pharmaceutically acceptable carriers.

\* \* \* \* \*